(12) United States Patent
Giard et al.

(10) Patent No.: US 8,692,026 B2
(45) Date of Patent: Apr. 8, 2014

(54) PROCESSES FOR PRODUCING 4-BROMO-2-METHOXYBENZALDEHYDE

(75) Inventors: Thierry J. Giard, Wavre (BE); Vincent L. Mutterer, Bousval (BE); Christophe Durvaux, Brussels (BE)

(73) Assignee: Albemarle Corporation, Baton Rouge, LA (US)

(*) Notice: Subject to any disclaimer, the term of this patent is extended or adjusted under 35 U.S.C. 154(b) by 0 days.

(21) Appl. No.: 13/805,218

(22) PCT Filed: Jul. 1, 2011

(86) PCT No.: PCT/US2011/042738
§ 371 (c)(1),
(2), (4) Date: Dec. 18, 2012

(87) PCT Pub. No.: WO2012/009173
PCT Pub. Date: Jan. 19, 2012

(65) Prior Publication Data
US 2013/0090498 A1   Apr. 11, 2013

Related U.S. Application Data

(60) Provisional application No. 61/364,599, filed on Jul. 15, 2010.

(51) Int. Cl.
*C07C 45/64* (2006.01)
*C07C 47/55* (2006.01)
(52) U.S. Cl.
USPC ............................. 568/436; 568/437; 568/438
(58) Field of Classification Search
CPC ........ C07C 45/45; C07C 45/46; C07C 407/55
USPC .......................................... 568/436, 437, 438
See application file for complete search history.

(56) References Cited

U.S. PATENT DOCUMENTS

2006/0025462 A1   2/2006   Dunn et al.

FOREIGN PATENT DOCUMENTS

| EP | 1253152 | 10/2002 |
|----|---------|---------|
| WO | 01/62704 | 8/2001 |
| WO | 2005/063756 | 7/2005 |
| WO | 2008/122534 | 10/2008 |

OTHER PUBLICATIONS

Dabrowski, et al., "Halogen-Lithium Exchange Between Substituted Dihalobenzenes and Butyllithium: Application to the Regioselective Synthesis of Functionalized Bromobenzaldehydes", Tetrahedron, 2005, pp. 6590-6595, vol. 61, Poland.
Iida, et al., "Tributylmagnesium Ate Complex-Mediated Novel Bromine-Magnesium Exchange Reaction for Melective Monosubstitution of Dibromoarenes", Tetrahedron Letters, 2001, pp. 4841-4844, vol. 42, Japan.

*Primary Examiner* — Sikarl Witherspoon
(74) *Attorney, Agent, or Firm* — Marcy M. Hoefling; James A. Jubinsky; Nathan C. Dunn

(57) ABSTRACT

A new synthesis of 4-bromo-2-methoxybenzaldehyde is reported from 1,4 dibromo 2-fluorobenzene. First, 2-fluoro-4-bromobenzaldehyde is prepared through metal halogen exchange and formylation with a formyl source at 0° C. After crystallization, this intermediate is reacted with methanol in the presence of potassium carbonate. Subsequently, 4-bromo-2-methoxy-benzaldehyde is crystallized.

8 Claims, No Drawings

PROCESSES FOR PRODUCING 4-BROMO-2-METHOXYBENZALDEHYDE

BACKGROUND

4-Bromo-2-methoxybenzardehyde is useful as an intermediate in the chemical industry.

Syntheses are described in the literature to yield 4-bromo-2-methoxybenzaldehyde. For example, 4-bromo-2-methoxybenzaldehyde has already been synthesized through the formylation of meta bromo anisole, however the selectivity is low (J. Org. Chem. 2007, 72, 9786 & European Journal of Medicinal Chemistry, 1986, 21(5), 397-402). It is also described as being synthesized through metal halogen exchange between 1,4-dibromo 2-methoxybenzene and butyl lithium in cryogenic conditions, i.e., at −78° C. in diethyl ether, which is not a suitable solvent for large scale (Tetrahedron 2005, 61, 6590-6595). On the other hand, Iida et al. reported the synthesis of the intermediate 2-fluoro-4-bromobenzaldehyde via metal halogen exchange between 1,4 dibromo-2-fluorobenzene and tributylmagnesium ate complex, which needs to be prepared from butyl magnesium chloride and butyl lithium, followed by the formylation with DMF in 92% yield (Tetrahedron Letters 2001, 42, 4841). Luo Zhiyong et al described the preparation of 4-bromo-2-methoxybenzaldehyde from 2-fluoro-4-bromobenzaldehyde through a $S_NAr$ reaction in the presence of sodium methoxide in a modest yield of 38%.

It would be beneficial to the pharmaceutical industry to have processes for producing 4-bromo-2-methoxybenzaldehyde that have good selectivity and that do not require the use of cryogenic conditions.

THE INVENTION

This invention meets the above-described needs by providing processes for synthesis of 4-bromo-2-methoxybenzaldehyde from 1,4 dibromo 2-fluorobenzene.

Processes of this invention comprise (i) combining at least 1,4-dibromo-2-fluorobenzene, isopropyl magnesium chloride, THF and a first solvent to form a first combination; (ii) combining at least the first combination, a formyl source, and a second solvent to form a second combination; (iii) crystallizing a first solid intermediate from the second combination using a crystallization agent; (iv) combining at least the solid intermediate, a third solvent comprising methanol, and a carbonate to form a third combination; (v) distilling substantially all of the third solvent from the third combination; (vi) combining the distilled third combination and isopropyl alcohol or one or more alkanes comprising heptane or to form a fourth combination; and (vii) yielding 4-bromo-2-methoxybenzaldehyde from the fourth combination. In processes of this invention, the first solvent of (i) can comprise toluene, methyl tert-butyl ether, 2-methyl, or one or more alkanes such as heptane, methyl cyclohexane, or hexane; the combining of (i) can be conducted between about 0° C. to about 5° C.; the second solvent of (ii) can comprise toluene, methyl tert-butyl ether, 2-methyl, or one or more alkanes such as heptane, methyl cyclohexane, or hexane; the combining of (ii) can be conducted between about 0° C. to about 5° C.; the formyl source of (ii) can comprise dimethyl formamide or N-formyl secondary amine; the crystallization agent of (iii) can comprise one or more alkanes such as heptane, cyclohexane, methyl cyclohexane, octane, pentane, or hexane; and/or the carbonate of (iv) can comprise potassium carbonate, sodium carbonate, or cesium carbonate.

For example, in a process according to this invention, 2-fluoro-4-bromobenzaldehyde can be prepared through metal halogen exchange and formylation with dimethylformamide ("DMF") at 0° C. After crystallization from heptane, this intermediate can be reacted with methanol in the presence of potassium carbonate. Subsequently, 4-bromo-2-methoxybenzaldehyde can be crystallized from heptane and finally obtained in 57% overall yield.

Optimized two-step processes for yielding 4-bromo-2-methoxybenzaldehyde from 1,4 dibromo-2-fluorobenzene are provided by this invention.

First, the metal halogen exchange between 1,4-dibromo-2-fluorobenzene and isopropyl magnesium chloride can be very selective at 0° C. and the formylation very efficient. After work up, the intermediate 4-bromo-2-fluorobenzaldehyde can be crystallized from heptane and finally obtained in 74% yield. Subsequently, to minimize any Cannizzaro reaction, that is largely observed using sodium methoxide as described by Luo Zhiyong et al, the $S_NAr$ reaction can be run in methanol at 50° C. in the presence of potassium carbonate. Finally, after work-up, 4-bromo-2-methoxybenzaldehyde can be purified in heptane and obtained in 57% overall yield.

The synthetic scheme for processes according to this invention is presented below:

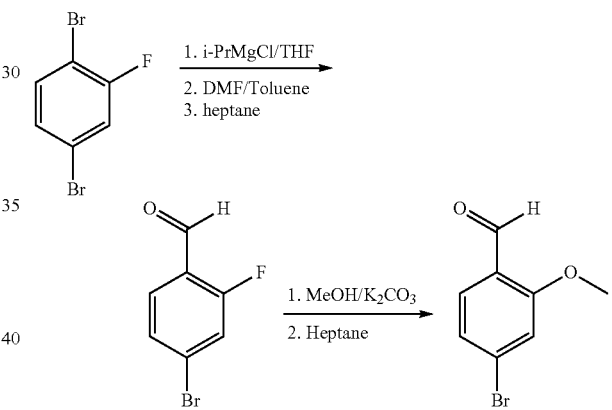

EXAMPLES

The following examples are illustrative of the principles of this invention. It is understood that this invention is not limited to any one specific embodiment exemplified herein, whether in the examples or the remainder of this patent application.

Example 1

(i) At ambient temperature, 2 M isopropyl magnesium chloride in THF (86 ml) is loaded into a flask;

(ii) The reaction mixture is cooled down to 0° C.;

(iii) A mixture of 1,4-dibromo-2-fluorobenzene (36.50 g) and THF (59.6 ml) is added to the reaction mixture between 0 and 5° C. over 30 min;

(iv) The reaction mixture is stirred for 1 hour;

(v) Between 0° C. and 5° C. a mixture of DMF (12.63 g) and toluene (12.63 ml) is added to the reaction mixture;

(vi) The reaction mixture is stirred for 4 hours;

(vii) A mixture of acetic acid (10.38 g) and water (37 ml) is prepared and cooled to 0° C.;

(viii) The reaction mixture is added to the prepared acetic acid/water mixture while keeping the temperature <10° C.;

(ix) Toluene (182.5 ml) is added to the reaction mixture;

(x) A phase cut is conducted (organic phase up);

(xi) The organic layer is washed with acetic acid (1.73 g) diluted in water (15 ml);

(xii) A phase cut is conducted (organic phase up);

(xiii) The organic layer is washed with water (15 ml) and a phase cut is conducted;

(xiv) Solvent is distilled off and heptane (78 ml) is added;

(xv) The reaction mixture is heated to 50° C. then slowly cooled down to ambient temperature;

(xvi) The reaction mixture is cooled to 0° C. and the solid is filtered off;

(xvii) The solid is rinsed with heptane (10 ml);

(xviii) The solid is dried at 40° C. under reduced pressure ($1^{st}$ crop);

(xix) The mother liquor is concentrated and heptane is added (13 ml);

(xx) The mixture is heated up to 50° C. and then cooled down to 0° C.;

(xxi) The solid is filtered off and rinsed with heptane (7 ml) ($2^{nd}$ crop);

(xxii) The solid is dried at 40° C. under reduced pressure;

(xxiii) 2-F-4-Bromobenzaldehyde (crop 1+crop 2) is loaded in a flask and methanol (105.9 ml) is added;

(xxiv) The 2-F-4-Bromobenzaldehyde/methanol mixture is heated to 50° C.;

(xxv) 2.87 g of potassium carbonate is added to the mixture every 45 min (×4);

(xxvi) Potassium carbonate (3.58 g) is added to the mixture;

(xxvii) The mixture is stirred overnight;

(xxviii) Solvent is distilled from the mixture and then methyl tert-butyl ether (150 ml) is added;

(xxix) Water (80 ml) is added and a phase cut (organic phase up) is conducted;

(xxx) Water (80 ml) is added and a phase cut (organic phase up) is conducted;

(xxxi) Solvent is distilled off;

(xxxii) Heptane (61 ml) is added;

(xxxiii) The mixture is heated up to 50° C. then cooled down to 0° C.;

(xxxiv) Solid is filtered off and rinsed with heptane (20 ml); and (xxxv) The solid is dried at 40° C. under reduced pressure.

Processes of this invention are advantageous over current processes. For example, the lowest temperature required is about 0° C., compared to −78° C. that is required with the butyl lithium process in diethyl ether described in Tetrahedron 2005, 61, 6590-6595. Also, processes of this invention enable performance of $S_NAr$ directly with 4-bromo-2-fluorobenzene and therefore avoid a protection/deportation sequence of the aldehyde moiety.

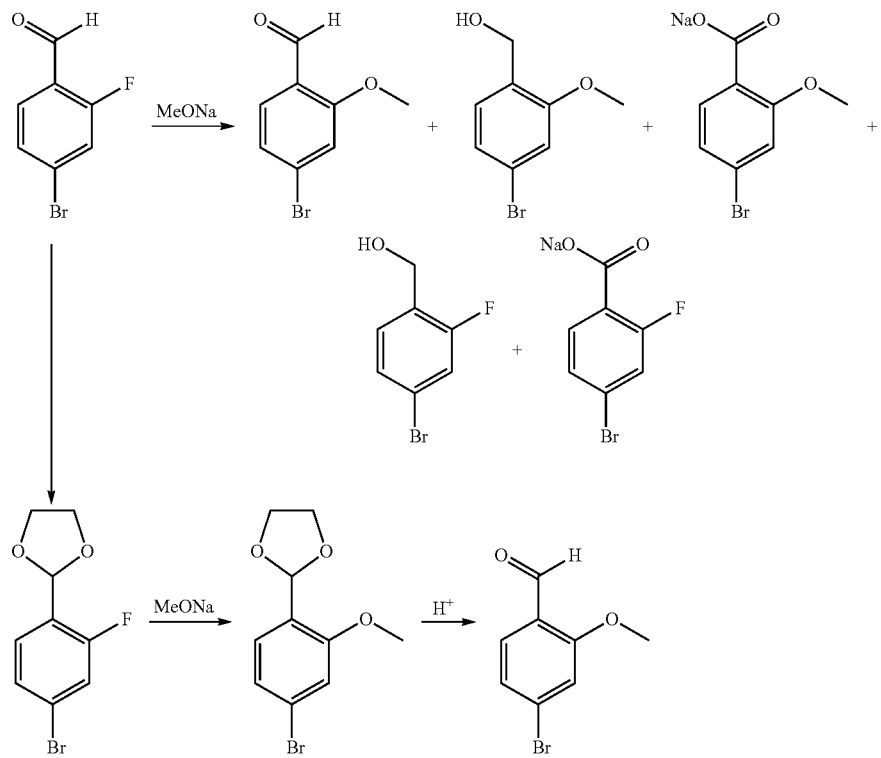

Regarding the synthesis of 2-fluoro-4-bromobenzaldehyde, Iida et al. reported the metal halogen exchange between 1,4 dibromo-2-fluorobenzene and tributylmagnesium ate complex followed by the formylation with DMF in 92% yield (Tetrahedron Letters 2001, 42, 4841). Using isopropyl magnesium chloride for the metal halogen exchange in processes of this invention is clearly an advantage over the use of tributylmagnesium ate complex since two equivalents of butyl lithium are required with butyl magnesium chloride. Additionally, processes of this invention do not require preparation of the reagents that will perform the metal halogen exchange since only isopropyl magnesium chloride is used. Avoiding the manipulation of butyl lithium, which is a very reactive reagent, is also advantageous.

It is to be understood that the reactants and components referred to by chemical name or formula anywhere in the specification or claims hereof, whether referred to in the singular or plural, are identified as they exist prior to being combined with or coming into contact with another substance referred to by chemical name or chemical type (e.g., another reactant, a solvent, or etc.). It matters not what chemical changes, transformations and/or reactions, if any, take place in the resulting combination or solution or reaction medium as such changes, transformations and/or reactions are the natural result of bringing the specified reactants and/or components together under the conditions called for pursuant to this disclosure. Thus the reactants and components are identified as ingredients to be brought together in connection with performing a desired chemical reaction or in forming a combination to be used in conducting a desired reaction. Accordingly, even though the claims hereinafter may refer to substances, components and/or ingredients in the present tense ("comprises", "is", etc.), the reference is to the substance, component or ingredient as it existed at the time just before it was first contacted, combined, blended or mixed with one or more other substances, components and/or ingredients in accordance with the present disclosure. Whatever transformations, if any, which occur in situ as a reaction is conducted is what the claim is intended to cover. Thus the fact that a substance, component or ingredient may have lost its original identity through a chemical reaction or transformation during the course of contacting, combining, blending or mixing operations, if conducted in accordance with this disclosure and with the application of common sense and the ordinary skill of a chemist, is thus wholly immaterial for an accurate understanding and appreciation of the true meaning and substance of this disclosure and the claims thereof. As will be familiar to those skilled in the art, the terms "combined", "combining", and the like as used herein mean that the components that are "combined" or that one is "combining" are put into a container with each other. Likewise a "combination" of components means the components having been put together in a container.

While the present invention has been described in terms of one or more preferred embodiments, it is to be understood that other modifications may be made without departing from the scope of the invention, which is set forth in the claims below.

What is claimed is:

1. A process comprising:
    (i) combining at least 1,4-dibromo-2-fluorobenzene, isopropyl magnesium chloride, THF and a first solvent to form a first combination;
    (ii) combining at least the first combination, a formyl source, and a second solvent to form a second combination;
    (iii) crystallizing a first solid intermediate from the second combination using a crystallization agent;
    (iv) combining at least the solid intermediate, a third solvent comprising methanol, and a carbonate to form a third combination;
    (v) distilling substantially all of the third solvent from the third combination;
    (vi) combining the distilled third combination and isopropyl alcohol or one or more alkanes comprising heptane or to form a fourth combination; and
    (vii) yielding 4-bromo-2-methoxybenzaldehyde from the fourth combination.

2. The process of claim 1 wherein the first solvent of (i) comprises toluene, methyl tent-butyl ether, 2-methyl, heptane, methyl cyclohexane, or hexane.

3. The process of claim 1 wherein the combining of (i) is conducted between about 0° C. to about 5° C.

4. The process of claim 1 wherein the second solvent of (ii) comprises toluene, methyl tert-butyl ether, 2-methyl, heptane, methyl cyclohexane, or hexane.

5. The process of claim 1 wherein the combining of (ii) is conducted between about 0° C. to about 5° C.

6. The process of claim 1 wherein the formyl source of (ii) comprises dimethyl formamide or N-formyl secondary amine.

7. The process of claim 1 wherein the crystallization agent of (iii) comprises heptane, cyclohexane, methyl cyclohexane, octane, pentane, or hexane.

8. The process of claim 1 wherein the carbonate of (iv) comprises potassium carbonate, sodium carbonate, or cesium carbonate.

* * * * *